(12) United States Patent
Williams (10) Patent No.: US 11,399,825 B2
(45) Date of Patent: Aug. 2, 2022

(54) RELOAD ASSEMBLY WITH KNIFE CARRIER LOCKOUT

(71) Applicant: Covidien LP, Mansfield, MA (US)

(72) Inventor: Justin Williams, Southbury, CT (US)

(73) Assignee: Covidien LP, Mansfield, MA (US)

( * ) Notice: Subject to any disclaimer, the term of this patent is extended or adjusted under 35 U.S.C. 154(b) by 109 days.

(21) Appl. No.: 16/665,570

(22) Filed: Oct. 28, 2019

(65) Prior Publication Data

US 2021/0121176 A1 Apr. 29, 2021

(51) Int. Cl.
*A61B 17/115* (2006.01)
*A61B 17/068* (2006.01)
*A61B 17/072* (2006.01)

(52) U.S. Cl.
CPC .............. *A61B 17/0684* (2013.01); *A61B 2017/07228* (2013.01); *A61B 2017/07271* (2013.01); *A61B 2017/07285* (2013.01)

(58) Field of Classification Search
CPC .............. A61B 17/115; A61B 17/1155; A61B 2017/07271; A61B 2017/07285
USPC ............................................. 227/175.1–182.1
See application file for complete search history.

(56) References Cited

U.S. PATENT DOCUMENTS

| | | |
|---|---|---|
| 3,193,165 A | 7/1965 | Akhalaya et al. |
| 3,388,847 A | 6/1968 | Kasulin et al. |
| 3,552,626 A | 1/1971 | Astafiev et al. |
| 3,638,652 A | 2/1972 | Kelley |
| 3,771,526 A | 11/1973 | Rudie |
| 4,198,982 A | 4/1980 | Fortner et al. |
| 4,207,898 A | 6/1980 | Becht |
| 4,289,133 A | 9/1981 | Rothfuss |
| 4,304,236 A | 12/1981 | Conta et al. |
| 4,319,576 A | 3/1982 | Rothfuss |
| 4,350,160 A | 9/1982 | Kolesov et al. |
| 4,351,466 A | 9/1982 | Noiles |
| 4,379,457 A | 4/1983 | Gravener et al. |
| 4,473,077 A | 9/1984 | Noiles et al. |
| 4,476,863 A | 10/1984 | Kanshin et al. |
| 4,485,817 A | 12/1984 | Swiggett |
| 4,488,523 A | 12/1984 | Shichman |
| 4,505,272 A | 3/1985 | Utyamyshev et al. |
| 4,505,414 A | 3/1985 | Filipi |
| 4,520,817 A | 6/1985 | Green |

(Continued)

FOREIGN PATENT DOCUMENTS

| CA | 908529 A | 8/1972 |
|---|---|---|
| CA | 2805365 A1 | 8/2013 |

(Continued)

OTHER PUBLICATIONS

European Search Report dated Mar. 29, 2021, corresponding to counterpart European Application No. 20204057.2; 11 pages.

*Primary Examiner* — Anna K Kinsaul
*Assistant Examiner* — Himchan Song
(74) *Attorney, Agent, or Firm* — Carter, DeLuca & Farrell LLP (57) ABSTRACT

A surgical stapling device includes a reload assembly that include at least one locking tab to retain a knife carrier of the reload assembly in a retracted position after the stapling device is fired. The at least one locking tab is disposed on the knife carrier and is configured to engage a stop surface of a staple actuator to prevent readvacement of the knife carrier relative to the staple actuator.

20 Claims, 8 Drawing Sheets

(56) References Cited

U.S. PATENT DOCUMENTS

| | | |
|---|---|---|
| 4,550,870 A | 11/1985 | Krumme et al. |
| 4,573,468 A | 3/1986 | Conta et al. |
| 4,576,167 A | 3/1986 | Noiles |
| 4,592,354 A | 6/1986 | Rothfuss |
| 4,603,693 A | 8/1986 | Conta et al. |
| 4,606,343 A | 8/1986 | Conta et al. |
| 4,632,290 A | 12/1986 | Green et al. |
| 4,646,745 A | 3/1987 | Noiles |
| 4,665,917 A | 5/1987 | Clanton et al. |
| 4,667,673 A | 5/1987 | Li |
| 4,671,445 A | 6/1987 | Barker et al. |
| 4,700,703 A | 10/1987 | Resnick et al. |
| 4,703,887 A | 11/1987 | Clanton et al. |
| 4,708,141 A | 11/1987 | Inoue et al. |
| 4,717,063 A | 1/1988 | Ebihara |
| 4,752,024 A | 6/1988 | Green et al. |
| 4,754,909 A | 7/1988 | Barker et al. |
| 4,776,506 A | 10/1988 | Green |
| 4,817,847 A | 4/1989 | Redtenbacher et al. |
| 4,873,977 A | 10/1989 | Avant et al. |
| 4,893,662 A | 1/1990 | Gervasi |
| 4,903,697 A | 2/1990 | Resnick et al. |
| 4,907,591 A | 3/1990 | Vasconcellos et al. |
| 4,917,114 A | 4/1990 | Green et al. |
| 4,957,499 A | 9/1990 | Lipatov et al. |
| 4,962,877 A | 10/1990 | Hervas |
| 5,005,749 A | 4/1991 | Aranyi |
| 5,042,707 A | 8/1991 | Taheri |
| 5,047,039 A | 9/1991 | Avant et al. |
| 5,104,025 A | 4/1992 | Main et al. |
| 5,119,983 A | 6/1992 | Green et al. |
| 5,122,156 A | 6/1992 | Granger et al. |
| 5,139,513 A | 8/1992 | Segato |
| 5,158,222 A | 10/1992 | Green et al. |
| 5,188,638 A | 2/1993 | Tzakis |
| 5,193,731 A | 3/1993 | Aranyi |
| 5,197,648 A | 3/1993 | Gingold |
| 5,197,649 A | 3/1993 | Bessler et al. |
| 5,205,459 A | 4/1993 | Brinkerhoff et al. |
| 5,221,036 A | 6/1993 | Takase |
| 5,222,963 A | 6/1993 | Brinkerhoff et al. |
| 5,253,793 A | 10/1993 | Green et al. |
| 5,261,920 A | 11/1993 | Main et al. |
| 5,271,543 A * | 12/1993 | Grant .................. A61B 17/115 227/179.1 |
| 5,271,544 A | 12/1993 | Fox et al. |
| 5,275,322 A | 1/1994 | Brinkerhoff et al. |
| 5,282,810 A | 2/1994 | Allen et al. |
| 5,285,944 A | 2/1994 | Green et al. |
| 5,285,945 A | 2/1994 | Brinkerhoff et al. |
| 5,292,053 A | 3/1994 | Bilotti et al. |
| 5,309,927 A | 5/1994 | Welch |
| 5,312,024 A | 5/1994 | Grant et al. |
| 5,314,435 A | 5/1994 | Green et al. |
| 5,314,436 A | 5/1994 | Wilk |
| 5,330,486 A | 7/1994 | Wilk |
| 5,333,773 A | 8/1994 | Main et al. |
| 5,344,059 A | 9/1994 | Green et al. |
| 5,346,115 A | 9/1994 | Perouse et al. |
| 5,348,259 A | 9/1994 | Blanco et al. |
| 5,350,104 A | 9/1994 | Main et al. |
| 5,355,897 A | 10/1994 | Pietrafitta et al. |
| 5,360,154 A | 11/1994 | Green |
| 5,368,215 A | 11/1994 | Green et al. |
| 5,392,979 A | 2/1995 | Green et al. |
| 5,395,030 A | 3/1995 | Kuramoto et al. |
| 5,403,333 A | 4/1995 | Kaster et al. |
| 5,404,870 A | 4/1995 | Brinkerhoff et al. |
| 5,411,508 A | 5/1995 | Bessler et al. |
| 5,425,738 A | 6/1995 | Gustafson et al. |
| 5,433,721 A | 7/1995 | Hooven et al. |
| 5,437,684 A | 8/1995 | Calabrese et al. |
| 5,439,156 A | 8/1995 | Grant et al. |
| 5,443,198 A | 8/1995 | Viola et al. |
| 5,447,514 A | 9/1995 | Gerry et al. |
| 5,454,825 A | 10/1995 | Van Leeuwen et al. |
| 5,464,415 A | 11/1995 | Chen |
| 5,470,006 A | 11/1995 | Rodak |
| 5,474,223 A | 12/1995 | Viola et al. |
| 5,497,934 A | 3/1996 | Brady et al. |
| 5,503,635 A | 4/1996 | Sauer et al. |
| 5,522,534 A | 6/1996 | Viola et al. |
| 5,533,661 A | 7/1996 | Main et al. |
| 5,588,579 A | 12/1996 | Schnut et al. |
| 5,609,285 A | 3/1997 | Grant et al. |
| 5,626,591 A | 5/1997 | Kockerling et al. |
| 5,632,433 A | 5/1997 | Grant et al. |
| 5,639,008 A | 6/1997 | Gallagher et al. |
| 5,641,111 A | 6/1997 | Ahrens et al. |
| 5,658,300 A | 8/1997 | Bito et al. |
| 5,669,918 A | 9/1997 | Balazs et al. |
| 5,685,474 A | 11/1997 | Seeber |
| 5,709,335 A | 1/1998 | Heck |
| 5,715,987 A | 2/1998 | Kelley et al. |
| 5,718,360 A | 2/1998 | Green et al. |
| 5,720,755 A | 2/1998 | Dakov |
| 5,732,872 A | 3/1998 | Bolduc et al. |
| 5,749,896 A | 5/1998 | Cook |
| 5,758,814 A | 6/1998 | Gallagher et al. |
| 5,799,857 A | 9/1998 | Robertson et al. |
| 5,814,055 A | 9/1998 | Knodel et al. |
| 5,833,698 A | 11/1998 | Hinchliffe et al. |
| 5,836,503 A | 11/1998 | Ehrenfels et al. |
| 5,839,639 A | 11/1998 | Sauer et al. |
| 5,855,312 A | 1/1999 | Toledano |
| 5,860,581 A | 1/1999 | Robertson et al. |
| 5,868,760 A | 2/1999 | McGuckin, Jr. |
| 5,881,943 A | 3/1999 | Heck et al. |
| 5,915,616 A | 6/1999 | Viola et al. |
| 5,947,363 A | 9/1999 | Bolduc et al. |
| 5,951,576 A | 9/1999 | Wakabayashi |
| 5,957,363 A | 9/1999 | Heck |
| 5,993,468 A | 11/1999 | Rygaard |
| 6,024,748 A | 2/2000 | Manzo et al. |
| 6,050,472 A | 4/2000 | Shibata |
| 6,053,390 A | 4/2000 | Green et al. |
| 6,068,636 A | 5/2000 | Chen |
| 6,083,241 A | 7/2000 | Longo et al. |
| 6,102,271 A | 8/2000 | Longo et al. |
| 6,117,148 A | 9/2000 | Ravo et al. |
| 6,119,913 A | 9/2000 | Adams et al. |
| 6,126,058 A | 10/2000 | Adams et al. |
| 6,142,933 A | 11/2000 | Longo et al. |
| 6,149,667 A | 11/2000 | Hovland et al. |
| 6,176,413 B1 | 1/2001 | Heck et al. |
| 6,179,195 B1 | 1/2001 | Adams et al. |
| 6,193,129 B1 | 2/2001 | Billner et al. |
| 6,203,553 B1 | 3/2001 | Robertson et al. |
| 6,209,773 B1 | 4/2001 | Bolduc et al. |
| 6,241,140 B1 | 6/2001 | Adams et al. |
| 6,253,984 B1 | 7/2001 | Heck et al. |
| 6,258,107 B1 | 7/2001 | Balazs et al. |
| 6,264,086 B1 | 7/2001 | McGuckin, Jr. |
| 6,269,997 B1 | 8/2001 | Balazs et al. |
| 6,273,897 B1 | 8/2001 | Dalessandro et al. |
| 6,279,809 B1 | 8/2001 | Nicolo |
| 6,302,311 B1 | 10/2001 | Adams et al. |
| 6,338,737 B1 | 1/2002 | Toledano |
| 6,343,731 B1 | 2/2002 | Adams et al. |
| 6,387,105 B1 | 5/2002 | Gifford, III et al. |
| 6,398,795 B1 | 6/2002 | McAlister et al. |
| 6,402,008 B1 | 6/2002 | Lucas |
| 6,439,446 B1 | 8/2002 | Perry et al. |
| 6,443,973 B1 | 9/2002 | Whitman |
| 6,450,390 B2 | 9/2002 | Heck et al. |
| 6,478,210 B2 | 11/2002 | Adams et al. |
| 6,488,197 B1 | 12/2002 | Whitman |
| 6,491,201 B1 | 12/2002 | Whitman |
| 6,494,877 B2 | 12/2002 | Odell et al. |
| 6,503,259 B2 | 1/2003 | Huxel et al. |
| 6,517,566 B1 | 2/2003 | Hovland et al. |
| 6,520,398 B2 | 2/2003 | Nicolo |
| 6,533,157 B1 | 3/2003 | Whitman |
| 6,551,334 B2 | 4/2003 | Blatter et al. |

(56) References Cited

U.S. PATENT DOCUMENTS

| | | |
|---|---|---|
| 6,578,751 B2 | 6/2003 | Hartwick |
| 6,585,144 B2 | 7/2003 | Adams et al. |
| 6,588,643 B2 | 7/2003 | Bolduc et al. |
| 6,592,596 B1 | 7/2003 | Geitz |
| 6,601,749 B2 | 8/2003 | Sullivan et al. |
| 6,605,078 B2 | 8/2003 | Adams |
| 6,605,098 B2 | 8/2003 | Nobis et al. |
| 6,626,921 B2 | 9/2003 | Blatter et al. |
| 6,629,630 B2 | 10/2003 | Adams |
| 6,631,837 B1 | 10/2003 | Heck |
| 6,632,227 B2 | 10/2003 | Adams |
| 6,632,237 B2 | 10/2003 | Ben-David et al. |
| 6,652,542 B2 | 11/2003 | Blatter et al. |
| 6,659,327 B2 | 12/2003 | Heck et al. |
| 6,676,671 B2 | 1/2004 | Robertson et al. |
| 6,681,979 B2 | 1/2004 | Whitman |
| 6,685,079 B2 | 2/2004 | Sharma et al. |
| 6,695,198 B2 | 2/2004 | Adams et al. |
| 6,695,199 B2 | 2/2004 | Whitman |
| 6,698,643 B2 | 3/2004 | Whitman |
| 6,716,222 B2 | 4/2004 | McAlister et al. |
| 6,716,233 B1 | 4/2004 | Whitman |
| 6,726,697 B2 | 4/2004 | Nicholas et al. |
| 6,742,692 B2 | 6/2004 | Hartwick |
| 6,743,244 B2 | 6/2004 | Blatter et al. |
| 6,763,993 B2 | 7/2004 | Bolduc et al. |
| 6,769,590 B2 | 8/2004 | Vresh et al. |
| 6,769,594 B2 | 8/2004 | Orban, III |
| 6,820,791 B2 | 11/2004 | Adams |
| 6,821,282 B2 | 11/2004 | Perry et al. |
| 6,827,246 B2 | 12/2004 | Sullivan et al. |
| 6,840,423 B2 | 1/2005 | Adams et al. |
| 6,843,403 B2 | 1/2005 | Whitman |
| 6,846,308 B2 | 1/2005 | Whitman et al. |
| 6,852,122 B2 | 2/2005 | Rush |
| 6,866,178 B2 | 3/2005 | Adams et al. |
| 6,872,214 B2 | 3/2005 | Sonnenschein et al. |
| 6,874,669 B2 | 4/2005 | Adams et al. |
| 6,884,250 B2 | 4/2005 | Monassevitch et al. |
| 6,905,504 B1 | 6/2005 | Vargas |
| 6,938,814 B2 | 9/2005 | Sharma et al. |
| 6,942,675 B1 | 9/2005 | Vargas |
| 6,945,444 B2 | 9/2005 | Gresham et al. |
| 6,953,138 B1 | 10/2005 | Dworak et al. |
| 6,957,758 B2 | 10/2005 | Aranyi |
| 6,959,851 B2 | 11/2005 | Heinrich |
| 6,978,922 B2 | 12/2005 | Bilotti et al. |
| 6,981,941 B2 | 1/2006 | Whitman et al. |
| 6,981,979 B2 | 1/2006 | Nicolo |
| 7,032,798 B2 | 4/2006 | Whitman et al. |
| 7,059,331 B2 | 6/2006 | Adams et al. |
| 7,059,510 B2 | 6/2006 | Orban, III |
| 7,077,856 B2 | 7/2006 | Whitman |
| 7,080,769 B2 | 7/2006 | Vresh et al. |
| 7,086,267 B2 | 8/2006 | Dworak et al. |
| 7,114,642 B2 | 10/2006 | Whitman |
| 7,118,528 B1 | 10/2006 | Piskun |
| 7,122,044 B2 | 10/2006 | Bolduc et al. |
| 7,128,748 B2 | 10/2006 | Mooradian et al. |
| 7,141,055 B2 | 11/2006 | Abrams et al. |
| 7,168,604 B2 | 1/2007 | Milliman et al. |
| 7,179,267 B2 | 2/2007 | Nolan et al. |
| 7,182,239 B1 | 2/2007 | Myers |
| 7,195,142 B2 | 3/2007 | Orban, III |
| 7,207,168 B2 | 4/2007 | Doepker et al. |
| 7,220,237 B2 | 5/2007 | Gannoe et al. |
| 7,234,624 B2 | 6/2007 | Gresham et al. |
| 7,235,089 B1 | 6/2007 | McGuckin, Jr. |
| RE39,841 E | 9/2007 | Bilotti et al. |
| 7,285,125 B2 | 10/2007 | Viola |
| 7,303,106 B2 | 12/2007 | Milliman et al. |
| 7,303,107 B2 | 12/2007 | Milliman et al. |
| 7,309,341 B2 | 12/2007 | Ortiz et al. |
| 7,322,994 B2 | 1/2008 | Nicholas et al. |
| 7,325,713 B2 | 2/2008 | Aranyi |
| 7,334,718 B2 | 2/2008 | McAlister et al. |
| 7,335,212 B2 | 2/2008 | Edoga et al. |
| 7,364,060 B2 | 4/2008 | Milliman |
| 7,398,908 B2 | 7/2008 | Holsten et al. |
| 7,399,305 B2 | 7/2008 | Csiky et al. |
| 7,401,721 B2 | 7/2008 | Holsten et al. |
| 7,401,722 B2 | 7/2008 | Hur |
| 7,407,075 B2 | 8/2008 | Holsten et al. |
| 7,410,086 B2 | 8/2008 | Ortiz et al. |
| 7,422,137 B2 | 9/2008 | Manzo |
| 7,422,138 B2 | 9/2008 | Bilotti et al. |
| 7,431,191 B2 | 10/2008 | Milliman |
| 7,438,718 B2 | 10/2008 | Milliman et al. |
| 7,455,676 B2 | 11/2008 | Holsten et al. |
| 7,455,682 B2 | 11/2008 | Viola |
| 7,481,347 B2 | 1/2009 | Roy |
| 7,494,038 B2 | 2/2009 | Milliman |
| 7,506,791 B2 | 3/2009 | Omaits et al. |
| 7,516,877 B2 | 4/2009 | Aranyi |
| 7,527,185 B2 | 5/2009 | Harari et al. |
| 7,537,602 B2 | 5/2009 | Whitman |
| 7,540,839 B2 | 6/2009 | Butler et al. |
| 7,546,939 B2 | 6/2009 | Adams et al. |
| 7,546,940 B2 | 6/2009 | Milliman et al. |
| 7,547,312 B2 | 6/2009 | Bauman et al. |
| 7,556,186 B2 | 7/2009 | Milliman |
| 7,559,451 B2 | 7/2009 | Sharma et al. |
| 7,585,306 B2 | 9/2009 | Abbott et al. |
| 7,588,174 B2 | 9/2009 | Holsten et al. |
| 7,600,663 B2 | 10/2009 | Green |
| 7,611,038 B2 | 11/2009 | Racenet et al. |
| 7,635,385 B2 | 12/2009 | Milliman et al. |
| 7,669,747 B2 | 3/2010 | Weisenburgh, II et al. |
| 7,686,201 B2 | 3/2010 | Csiky |
| 7,694,864 B2 | 4/2010 | Okada et al. |
| 7,699,204 B2 | 4/2010 | Viola |
| 7,708,181 B2 | 5/2010 | Cole et al. |
| 7,717,313 B2 | 5/2010 | Criscuolo et al. |
| 7,721,932 B2 | 5/2010 | Cole et al. |
| 7,726,539 B2 | 6/2010 | Holsten et al. |
| 7,743,958 B2 | 6/2010 | Orban, III |
| 7,744,627 B2 | 6/2010 | Orban, III et al. |
| 7,770,776 B2 | 8/2010 | Chen et al. |
| 7,771,440 B2 | 8/2010 | Ortiz et al. |
| 7,776,060 B2 | 8/2010 | Mooradian et al. |
| 7,793,813 B2 | 9/2010 | Bettuchi |
| 7,802,712 B2 | 9/2010 | Milliman et al. |
| 7,823,592 B2 | 11/2010 | Bettuchi et al. |
| 7,837,079 B2 | 11/2010 | Holsten et al. |
| 7,837,080 B2 | 11/2010 | Schwemberger |
| 7,837,081 B2 | 11/2010 | Holsten et al. |
| 7,845,536 B2 | 12/2010 | Viola et al. |
| 7,845,538 B2 | 12/2010 | Whitman |
| 7,857,187 B2 | 12/2010 | Milliman |
| 7,886,951 B2 | 2/2011 | Hessler |
| 7,896,215 B2 | 3/2011 | Adams et al. |
| 7,900,806 B2 | 3/2011 | Chen et al. |
| 7,909,039 B2 | 3/2011 | Hur |
| 7,909,219 B2 | 3/2011 | Cole et al. |
| 7,909,222 B2 | 3/2011 | Cole et al. |
| 7,909,223 B2 | 3/2011 | Cole et al. |
| 7,913,892 B2 | 3/2011 | Cole et al. |
| 7,918,377 B2 | 4/2011 | Measamer et al. |
| 7,922,062 B2 | 4/2011 | Cole et al. |
| 7,922,743 B2 | 4/2011 | Heinrich et al. |
| 7,931,183 B2 | 4/2011 | Orban, III |
| 7,938,307 B2 | 5/2011 | Bettuchi |
| 7,942,302 B2 | 5/2011 | Roby et al. |
| 7,951,166 B2 | 5/2011 | Orban, III et al. |
| 7,959,050 B2 | 6/2011 | Smith et al. |
| 7,967,181 B2 | 6/2011 | Viola et al. |
| 7,975,895 B2 | 7/2011 | Milliman |
| 8,002,795 B2 | 8/2011 | Beetel |
| 8,006,701 B2 | 8/2011 | Bilotti et al. |
| 8,006,889 B2 | 8/2011 | Adams et al. |
| 8,011,551 B2 | 9/2011 | Marczyk et al. |
| 8,011,554 B2 | 9/2011 | Milliman |
| 8,016,177 B2 | 9/2011 | Bettuchi et al. |
| 8,016,858 B2 | 9/2011 | Whitman |

(56) References Cited

U.S. PATENT DOCUMENTS

| | | |
|---|---|---|
| 8,020,741 B2 | 9/2011 | Cole et al. |
| 8,025,199 B2 | 9/2011 | Whitman et al. |
| 8,028,885 B2 | 10/2011 | Smith et al. |
| 8,038,046 B2 | 10/2011 | Smith et al. |
| 8,043,207 B2 | 10/2011 | Adams |
| 8,066,167 B2 | 11/2011 | Measamer et al. |
| 8,066,169 B2 | 11/2011 | Viola |
| 8,070,035 B2 | 12/2011 | Holsten et al. |
| 8,070,037 B2 | 12/2011 | Csiky |
| 8,096,458 B2 | 1/2012 | Hessler |
| 8,109,426 B2 | 2/2012 | Milliman et al. |
| 8,109,427 B2 | 2/2012 | Orban, III |
| 8,113,405 B2 | 2/2012 | Milliman |
| 8,113,406 B2 | 2/2012 | Holsten et al. |
| 8,113,407 B2 | 2/2012 | Holsten et al. |
| 8,123,103 B2 | 2/2012 | Milliman |
| 8,128,645 B2 | 3/2012 | Sonnenschein et al. |
| 8,132,703 B2 | 3/2012 | Milliman et al. |
| 8,136,712 B2 | 3/2012 | Zingman |
| 8,146,790 B2 | 4/2012 | Milliman |
| 8,146,791 B2 | 4/2012 | Bettuchi et al. |
| 8,181,838 B2 | 5/2012 | Milliman et al. |
| 8,192,460 B2 | 6/2012 | Orban, III et al. |
| 8,201,720 B2 | 6/2012 | Hessler |
| 8,203,782 B2 | 6/2012 | Brueck et al. |
| 8,211,130 B2 | 7/2012 | Viola |
| 8,225,799 B2 | 7/2012 | Bettuchi |
| 8,225,981 B2 | 7/2012 | Criscuolo et al. |
| 8,231,041 B2 | 7/2012 | Marczyk et al. |
| 8,231,042 B2 | 7/2012 | Hessler et al. |
| 8,257,391 B2 | 9/2012 | Orban, III et al. |
| 8,267,301 B2 | 9/2012 | Milliman et al. |
| 8,272,552 B2 | 9/2012 | Holsten et al. |
| 8,276,802 B2 | 10/2012 | Kostrzewski |
| 8,281,975 B2 | 10/2012 | Criscuolo et al. |
| 8,286,845 B2 | 10/2012 | Perry et al. |
| 8,308,045 B2 | 11/2012 | Bettuchi et al. |
| 8,312,885 B2 | 11/2012 | Bettuchi et al. |
| 8,313,014 B2 | 11/2012 | Bettuchi |
| 8,317,073 B2 | 11/2012 | Milliman et al. |
| 8,317,074 B2 | 11/2012 | Ortiz et al. |
| 8,322,590 B2 | 12/2012 | Patel et al. |
| 8,328,060 B2 | 12/2012 | Jankowski et al. |
| 8,328,062 B2 | 12/2012 | Viola |
| 8,328,063 B2 | 12/2012 | Milliman et al. |
| 8,343,185 B2 | 1/2013 | Milliman et al. |
| 8,353,438 B2 | 1/2013 | Baxter, III et al. |
| 8,353,439 B2 | 1/2013 | Baxter, III et al. |
| 8,353,930 B2 | 1/2013 | Heinrich et al. |
| 8,360,295 B2 | 1/2013 | Milliman et al. |
| 8,365,974 B2 | 2/2013 | Milliman |
| 8,403,942 B2 | 3/2013 | Milliman et al. |
| 8,408,441 B2 | 4/2013 | Wenchell et al. |
| 8,413,870 B2 | 4/2013 | Pastorelli et al. |
| 8,413,872 B2 | 4/2013 | Patel |
| 8,418,905 B2 | 4/2013 | Milliman |
| 8,418,909 B2 | 4/2013 | Kostrzewski |
| 8,424,535 B2 | 4/2013 | Hessler et al. |
| 8,424,741 B2 | 4/2013 | McGuckin, Jr. et al. |
| 8,430,291 B2 | 4/2013 | Heinrich et al. |
| 8,430,292 B2 | 4/2013 | Patel et al. |
| 8,453,910 B2 | 6/2013 | Bettuchi et al. |
| 8,453,911 B2 | 6/2013 | Milliman et al. |
| 8,485,414 B2 | 7/2013 | Criscuolo et al. |
| 8,490,853 B2 | 7/2013 | Criscuolo et al. |
| 8,511,533 B2 | 8/2013 | Viola et al. |
| 8,551,138 B2 | 10/2013 | Orban, III et al. |
| 8,567,655 B2 | 10/2013 | Nalagatla et al. |
| 8,579,178 B2 | 11/2013 | Holsten et al. |
| 8,590,763 B2 | 11/2013 | Milliman |
| 8,590,764 B2 | 11/2013 | Hartwick et al. |
| 8,608,047 B2 | 12/2013 | Holsten et al. |
| 8,616,428 B2 | 12/2013 | Milliman et al. |
| 8,616,429 B2 | 12/2013 | Viola |
| 8,622,275 B2 | 1/2014 | Baxter, III et al. |
| 8,631,993 B2 | 1/2014 | Kostrzewski |
| 8,636,187 B2 | 1/2014 | Hueil et al. |
| 8,640,940 B2 | 2/2014 | Ohdaira |
| 8,662,370 B2 | 3/2014 | Takei |
| 8,663,258 B2 | 3/2014 | Bettuchi et al. |
| 8,672,931 B2 | 3/2014 | Goldboss et al. |
| 8,678,264 B2 | 3/2014 | Racenet et al. |
| 8,684,248 B2 | 4/2014 | Milliman |
| 8,684,250 B2 | 4/2014 | Bettuchi et al. |
| 8,684,251 B2 | 4/2014 | Rebuffat et al. |
| 8,684,252 B2 | 4/2014 | Patel et al. |
| 8,733,611 B2 | 5/2014 | Milliman |
| 9,023,014 B2 | 5/2015 | Chowaniec et al. |
| 9,055,943 B2 | 6/2015 | Zemlok et al. |
| 9,962,159 B2 | 5/2018 | Heinrich et al. |
| 2003/0111507 A1 | 6/2003 | Nunez |
| 2004/0073090 A1 | 4/2004 | Butler et al. |
| 2005/0051597 A1 | 3/2005 | Toledano |
| 2005/0107813 A1 | 5/2005 | Gilete Garcia |
| 2006/0000869 A1 | 1/2006 | Fontayne |
| 2006/0011698 A1 | 1/2006 | Okada et al. |
| 2006/0201989 A1 | 9/2006 | Ojeda |
| 2007/0027473 A1 | 2/2007 | Vresh et al. |
| 2007/0029363 A1 | 2/2007 | Popov |
| 2007/0060952 A1 | 3/2007 | Roby et al. |
| 2009/0236392 A1 | 9/2009 | Cole et al. |
| 2009/0236398 A1 | 9/2009 | Cole et al. |
| 2009/0236401 A1 | 9/2009 | Cole et al. |
| 2010/0019016 A1 | 1/2010 | Edoga et al. |
| 2010/0051668 A1 | 3/2010 | Milliman et al. |
| 2010/0084453 A1 | 4/2010 | Hu |
| 2010/0147923 A1 | 6/2010 | D'Agostino et al. |
| 2010/0163598 A1 | 7/2010 | Belzer |
| 2010/0224668 A1 | 9/2010 | Fontayne et al. |
| 2010/0230465 A1 | 9/2010 | Smith et al. |
| 2010/0258611 A1 | 10/2010 | Smith et al. |
| 2010/0264195 A1 | 10/2010 | Bettuchi |
| 2010/0327041 A1 | 12/2010 | Milliman et al. |
| 2011/0011916 A1 | 1/2011 | Levine |
| 2011/0114697 A1 | 5/2011 | Baxter, III et al. |
| 2011/0114700 A1 | 5/2011 | Baxter, III et al. |
| 2011/0144640 A1 | 6/2011 | Heinrich et al. |
| 2011/0147432 A1 | 6/2011 | Heinrich et al. |
| 2011/0174099 A1* | 7/2011 | Ross .............. A61B 17/072 74/89.32 |
| 2011/0192882 A1 | 8/2011 | Hess et al. |
| 2012/0145755 A1 | 6/2012 | Kahn |
| 2012/0193395 A1 | 8/2012 | Pastorelli et al. |
| 2012/0193398 A1 | 8/2012 | Williams et al. |
| 2012/0232339 A1 | 9/2012 | Csiky |
| 2012/0273548 A1 | 11/2012 | Ma et al. |
| 2012/0325888 A1 | 12/2012 | Qiao et al. |
| 2013/0015232 A1 | 1/2013 | Smith et al. |
| 2013/0020372 A1 | 1/2013 | Jankowski et al. |
| 2013/0020373 A1 | 1/2013 | Smith et al. |
| 2013/0032628 A1 | 2/2013 | Li et al. |
| 2013/0056516 A1 | 3/2013 | Viola |
| 2013/0060258 A1 | 3/2013 | Giacomantonio |
| 2013/0105544 A1 | 5/2013 | Mozdzierz et al. |
| 2013/0105546 A1 | 5/2013 | Milliman et al. |
| 2013/0105551 A1 | 5/2013 | Zingman |
| 2013/0126580 A1 | 5/2013 | Smith et al. |
| 2013/0153630 A1 | 6/2013 | Miller et al. |
| 2013/0153631 A1 | 6/2013 | Vasudevan et al. |
| 2013/0153633 A1 | 6/2013 | Casasanta, Jr. et al. |
| 2013/0153634 A1 | 6/2013 | Carter et al. |
| 2013/0153638 A1 | 6/2013 | Carter et al. |
| 2013/0153639 A1 | 6/2013 | Hodgkinson et al. |
| 2013/0175315 A1 | 7/2013 | Milliman |
| 2013/0175318 A1 | 7/2013 | Felder et al. |
| 2013/0175319 A1 | 7/2013 | Felder et al. |
| 2013/0175320 A1 | 7/2013 | Mandakolathur Vasudevan et al. |
| 2013/0181035 A1* | 7/2013 | Milliman .............. A61B 17/068 227/180.1 |
| 2013/0181036 A1* | 7/2013 | Olson .................. A61B 17/068 227/180.1 |
| 2013/0186930 A1 | 7/2013 | Wenchell et al. |
| 2013/0193185 A1 | 8/2013 | Patel |
| 2013/0193187 A1 | 8/2013 | Milliman |

(56) References Cited

U.S. PATENT DOCUMENTS

| | | |
|---|---|---|
| 2013/0193190 A1 | 8/2013 | Carter et al. |
| 2013/0193191 A1 | 8/2013 | Stevenson et al. |
| 2013/0193192 A1 | 8/2013 | Casasanta, Jr. et al. |
| 2013/0200131 A1* | 8/2013 | Racenet .............. A61B 17/072 227/180.1 |
| 2013/0206816 A1 | 8/2013 | Penna |
| 2013/0214027 A1 | 8/2013 | Hessler et al. |
| 2013/0214028 A1 | 8/2013 | Patel et al. |
| 2013/0228609 A1 | 9/2013 | Kostrzewski |
| 2013/0240597 A1 | 9/2013 | Milliman et al. |
| 2013/0240600 A1 | 9/2013 | Bettuchi |
| 2013/0248581 A1 | 9/2013 | Smith et al. |
| 2013/0277411 A1 | 10/2013 | Hodgkinson et al. |
| 2013/0277412 A1 | 10/2013 | Gresham et al. |
| 2013/0284792 A1 | 10/2013 | Ma |
| 2013/0292449 A1 | 11/2013 | Bettuchi et al. |
| 2013/0299553 A1 | 11/2013 | Mozdzierz |
| 2013/0299554 A1 | 11/2013 | Mozdzierz |
| 2013/0306701 A1 | 11/2013 | Olson |
| 2013/0306707 A1 | 11/2013 | Viola et al. |
| 2014/0008413 A1 | 1/2014 | Williams |
| 2014/0012317 A1 | 1/2014 | Orban et al. |
| 2016/0143641 A1 | 5/2016 | Sapienza et al. |
| 2016/0157856 A1 | 6/2016 | Williams et al. |
| 2016/0174988 A1 | 6/2016 | D'Agostino et al. |
| 2016/0302792 A1 | 10/2016 | Motai |
| 2017/0340351 A1 | 11/2017 | Sgroi, Jr. |
| 2017/0360445 A1* | 12/2017 | Milliman ............ A61B 17/1155 |
| 2018/0125495 A1 | 5/2018 | Sgroi, Jr. |
| 2019/0216462 A1 | 7/2019 | Milliman |
| 2021/0022731 A1* | 1/2021 | Eisinger ............. A61B 17/1155 |

FOREIGN PATENT DOCUMENTS

| | | |
|---|---|---|
| DE | 1057729 B | 5/1959 |
| DE | 3301713 A1 | 7/1984 |
| EP | 0152382 A2 | 8/1985 |
| EP | 0173451 A1 | 3/1986 |
| EP | 0190022 A2 | 8/1986 |
| EP | 0282157 A1 | 9/1988 |
| EP | 0503689 A2 | 9/1992 |
| EP | 1354560 A2 | 10/2003 |
| EP | 2138118 A2 | 12/2009 |
| EP | 2168510 A1 | 3/2010 |
| EP | 2238926 A2 | 10/2010 |
| EP | 2524656 A2 | 11/2012 |
| EP | 3730067 A1 | 10/2020 |
| EP | 3769698 A2 | 1/2021 |
| FR | 1136020 A | 5/1957 |
| FR | 1461464 A | 2/1966 |
| FR | 1588250 A | 4/1970 |
| FR | 2443239 A1 | 7/1980 |
| GB | 1185292 A | 3/1970 |
| GB | 2016991 A | 9/1979 |
| GB | 2070499 A | 9/1981 |
| JP | 2004147969 A | 5/2004 |
| JP | 2013138860 A | 7/2013 |
| NL | 7711347 A | 4/1979 |
| SU | 1509052 A1 | 9/1989 |
| WO | 8706448 A1 | 11/1987 |
| WO | 8900406 A1 | 1/1989 |
| WO | 9006085 A1 | 6/1990 |
| WO | 98/35614 A1 | 8/1998 |
| WO | 0154594 A1 | 8/2001 |
| WO | 2008107918 A1 | 9/2008 |

* cited by examiner

RELOAD ASSEMBLY WITH KNIFE CARRIER LOCKOUT

FIELD

The disclosure is directed to circular stapling devices and, more particularly, to reload assemblies for circular stapling devices with structure to retain a knife carrier of the reload assembly in a retracted position after the stapling device is fired.

BACKGROUND

Conventional circular stapling devices include an elongate body and a shell or reload assembly that is supported on a distal portion of the elongate body. The reload assembly includes a shell housing, a staple cartridge having a plurality of staples supported on the shell housing, a pusher assembly, a knife defining a cylindrical cavity, and a knife carrier that supports the knife. The pusher assembly includes an annular pusher and a staple pushing member that is engaged with the annular pusher and is movable to move the staple pushing member to eject staples from the staple cartridge. The knife carrier is movable to advance the knife through the staple cartridge to core or cut tissue.

After a stapling device has been operated to staple and cut tissue, the knife carrier and the knife are retracted to withdraw the knife into the shell housing. This serves two purposes. The first purpose is to move the knife to a position to allow removal of a tissue donut from within the cavity defined by the knife. The second purpose is to position the knife in a location recessed within the shell housing to avoid injury to a clinician during manipulation and disposal of the reload assembly.

In some instances, the tissue donut is compressed within the cavity defined by the knife to such a degree that removal of the tissue donut from within the cavity defined by the knife is difficult. A continuing need exists in the art for a reload assembly that includes improved structure for retaining the knife/knife carrier in a retracted position.

SUMMARY

A surgical stapling device includes an adaptor assembly having a proximal end portion and a distal end portion, and a reload assembly supported on the distal end portion of the adaptor assembly. The reload assembly includes a shell housing and a staple cartridge supporting a plurality of staples supported on the shell housing. The shell housing include an outer housing portion and an inner housing portion. The inner and outer housing portions defining an annular cavity therebetween. A staple pusher is supported within the annular cavity of the shell housing and is movable from a retracted position to an advanced position to eject staples from the staple cartridge. A staple actuator is supported within the annular cavity of the shell housing and has a stop surface. The staple actuator is positioned to engage the staple pusher and is movable from a retracted position to an advanced position to move the staple pusher from its retracted position to its advanced position. The staple actuator and the staple pusher define a through bore. A knife carrier is supported within the through bore and is movable between a retracted position and an advanced position. The knife carrier defines a longitudinal axis and includes at least one locking tab. The at least one locking tab is positioned proximally of the stop surface on the staple actuator when the staple actuator is in its advanced position and the knife carrier is in its retracted position to prevent readvancement of the knife carrier. A knife is supported on the knife carrier.

In embodiments, the surgical stapling device further includes a handle assembly, the proximal end portion of the adaptor assembly being supported on the handle assembly. The at least one locking tab of the knife carrier may be positioned distally of the stop surface of the staple actuator when the staple actuator and the knife carrier are in their retracted positions.

In some embodiments, the knife carrier includes at least one hook member. The at least one hook member may be aligned with the stop surface of the staple actuator such that the staple actuator maintains the knife carrier within the shell housing. The at least one hook member may be aligned with the stop surface of the staple actuator to prevent advancement of the knife carrier prior to advancement of the staple actuator. The at least one locking tab may be disposed on the at least one hook member distal of the proximal end.

In embodiments, the at least one locking tab includes an angled surface and the staple actuator may include an angled inner surface. Engagement of the angled surface of the at least one locking tab with the angled inner surface of the staple actuator may deflect the at least one hook member radial inward. Engagement of the stop surface with the locking surfaces may prevent advancement of the knife carrier.

In some embodiments, the surgical stapling device includes a coupling mechanism configured to couple the reload assembly to an adaptor assembly to facilitate release of the reload assembly from the adaptor assembly.

A reload assembly for a surgical stapling device includes a shell housing and a staple cartridge supporting a plurality of staples supported on the shell housing. The shell housing includes an outer housing portion and an inner housing portion. The inner and outer housing portions define an annular cavity therebetween. A staple pusher is supported within the annular cavity of the shell housing and is movable from a retracted position to an advanced position to eject staples from the staple cartridge. A staple actuator is supported within the annular cavity of the shell housing and has a stop surface. The staple actuator is positioned to engage the staple pusher and is movable from a retracted position to an advanced position to move the staple pusher from its retracted position to its advanced position. The staple actuator and the staple pusher define a through bore. A knife carrier is supported within the through bore and is movable between a retracted position and an advanced position, the knife carrier defining a longitudinal axis and including at least one locking tab, the at least one locking tab positioned distally of the stop surface on the staple actuator when the staple actuator is in its retracted position to permit advancement of the knife carrier and positioned proximally of the stop surface on the staple actuator when the staple actuator is in its advanced position and the knife carrier is in its retracted position to prevent readvancement of the knife carrier. A knife is supported on the knife carrier.

In embodiments, the knife carrier includes at least one hook member. The at least one hook member may be aligned with the stop surface of the staple actuator such that the staple actuator maintains the knife carrier within the shell housing. The at least one hook member may be aligned with the stop surface of the staple actuator to prevent advancement of the knife carrier prior to advancement of the staple actuator. The at least one locking tab may be disposed on the at least one hook member distal of the proximal end.

In embodiments, the at least one locking tab includes an angled surface and the staple actuator includes an angled inner surface. Engagement of the angled surface of the at least one locking tab with the angled inner surface of the staple actuator may deflect the at least one hook member radial inward. The at least one locking tab may include a locking surface. Engagement of the stop surface with the locking surfaces may prevent advancement of the knife carrier In some embodiments, the reload assembly includes a coupling mechanism configured to couple the reload assembly to an adaptor assembly of the surgical stapling device to facilitate release of the reload assembly from the adaptor assembly.

BRIEF DESCRIPTION OF THE DRAWINGS

Various embodiments of the disclosed reload assembly for a surgical stapling device are described herein below with reference to the drawings, wherein.

DETAILED DESCRIPTION

The disclosed reload assembly for a surgical stapling device will now be described in detail with reference to the drawings in which like reference numerals designate identical or corresponding elements in each of the several views. However, it is to be understood that the disclosed embodiments are merely exemplary of the disclosure and may be embodied in various forms. Well-known functions or constructions are not described in detail to avoid obscuring the disclosure in unnecessary detail. Therefore, specific structural and functional details disclosed herein are not to be interpreted as limiting, but merely as a basis for the claims and as a representative basis for teaching one skilled in the art to variously employ the disclosure in virtually any appropriately detailed structure. In addition, directional terms such as front, rear, upper, lower, top, bottom, distal, proximal, and similar terms are used to assist in understanding the description and are not intended to limit the disclosure.

In this description, the term "proximal" is used generally to refer to that portion of the device that is closer to a clinician, while the term "distal" is used generally to refer to that portion of the device that is farther from the clinician. In addition, the term "clinician" is used generally to refer to medical personnel including doctors, nurses, and support personnel.

Figure 1:
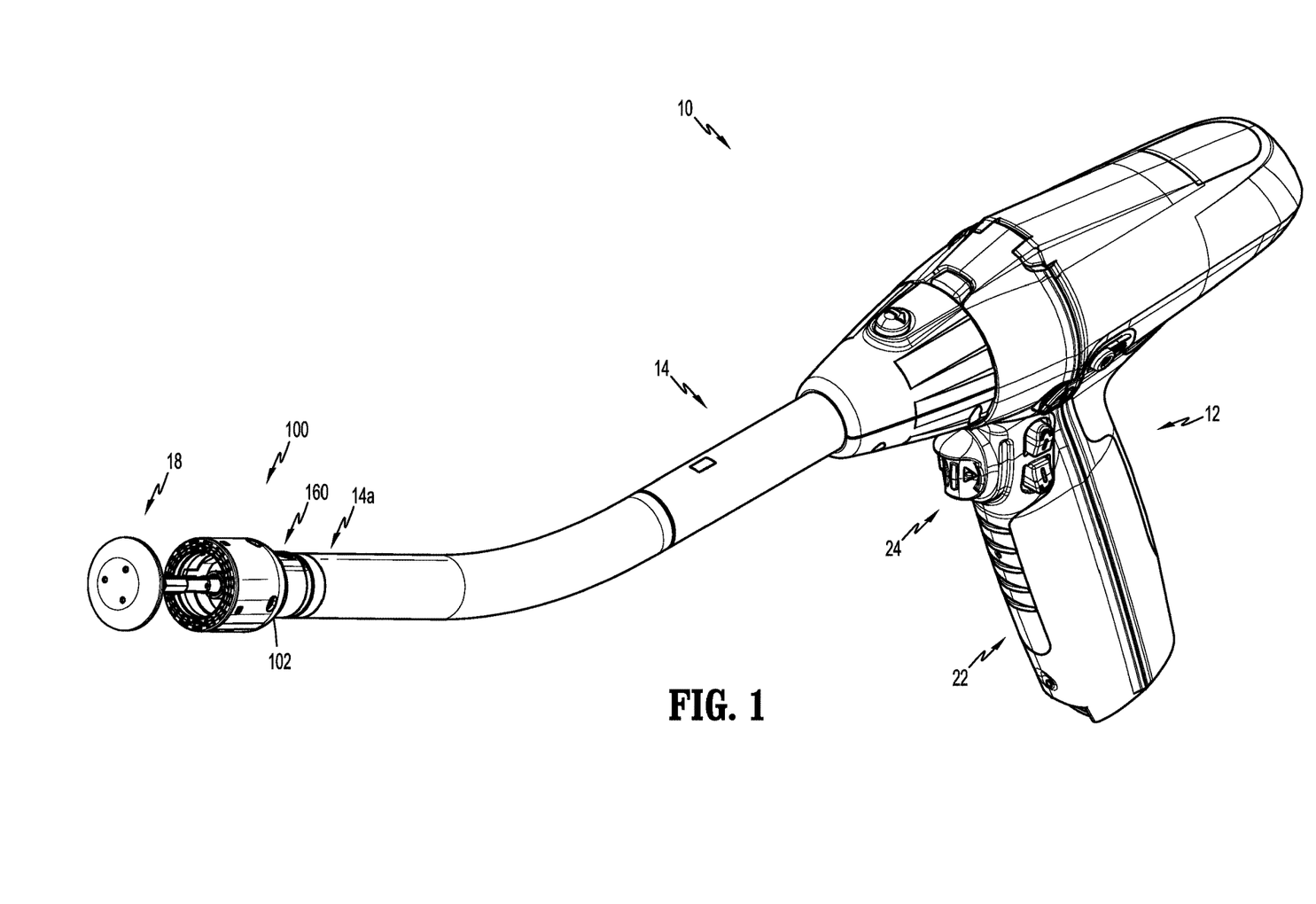
FIG. 1 is a side perspective view of a surgical stapling device including an exemplary embodiment of the disclosed reload assembly with the stapling device in a clamped position.

FIG. 1 illustrated a circular stapling device 10 including an exemplary embodiment of the disclosed reload assembly shown generally as reload assembly 100. The stapling device 10 includes a handle assembly 12, an elongate body or adaptor assembly 14, the reload assembly 100, and an anvil assembly 18 that is supported for movement in relation to the reload assembly 100 between spaced and approximated positions as is known in the art. In embodiments, the reload assembly 100 includes a proximal portion 102 that is releasably coupled to a distal portion 14a of the adaptor assembly 14. In some embodiments, the handle assembly 12 includes a stationary grip 22 that supports actuation buttons 24 for controlling operation of various functions of the stapling device 10 including approximation of the reload and anvil assemblies 100 and 18, respectively, firing of staples from the reload assembly 100, and cutting or coring of tissue.

The stapling device 10 is illustrated as an electrically powered stapling device including an electrically powered handle assembly 12 that may support one or more batteries (not shown). The adaptor assembly 14 is in the form of an adaptor assembly that translates power from the handle assembly 12 to the reload and anvil assemblies 100, 18, respectively. Examples of electrically powered stapling devices can be found in U.S. Pat. Nos. 9,055,943, 9,023,014, and U.S. Publication Nos. 2018/0125495, and 2017/0340351. Alternately, it is envisioned that the reload assembly could also be incorporated into a manually powered stapling device such as disclosed in U.S. Pat. No. 7,303,106 (the '106 patent) or a stapling device that is configured for use with a robotic system such as disclosed in U.S. Pat. No. 9,962,159 that does not include a handle assembly.

Figure 2:
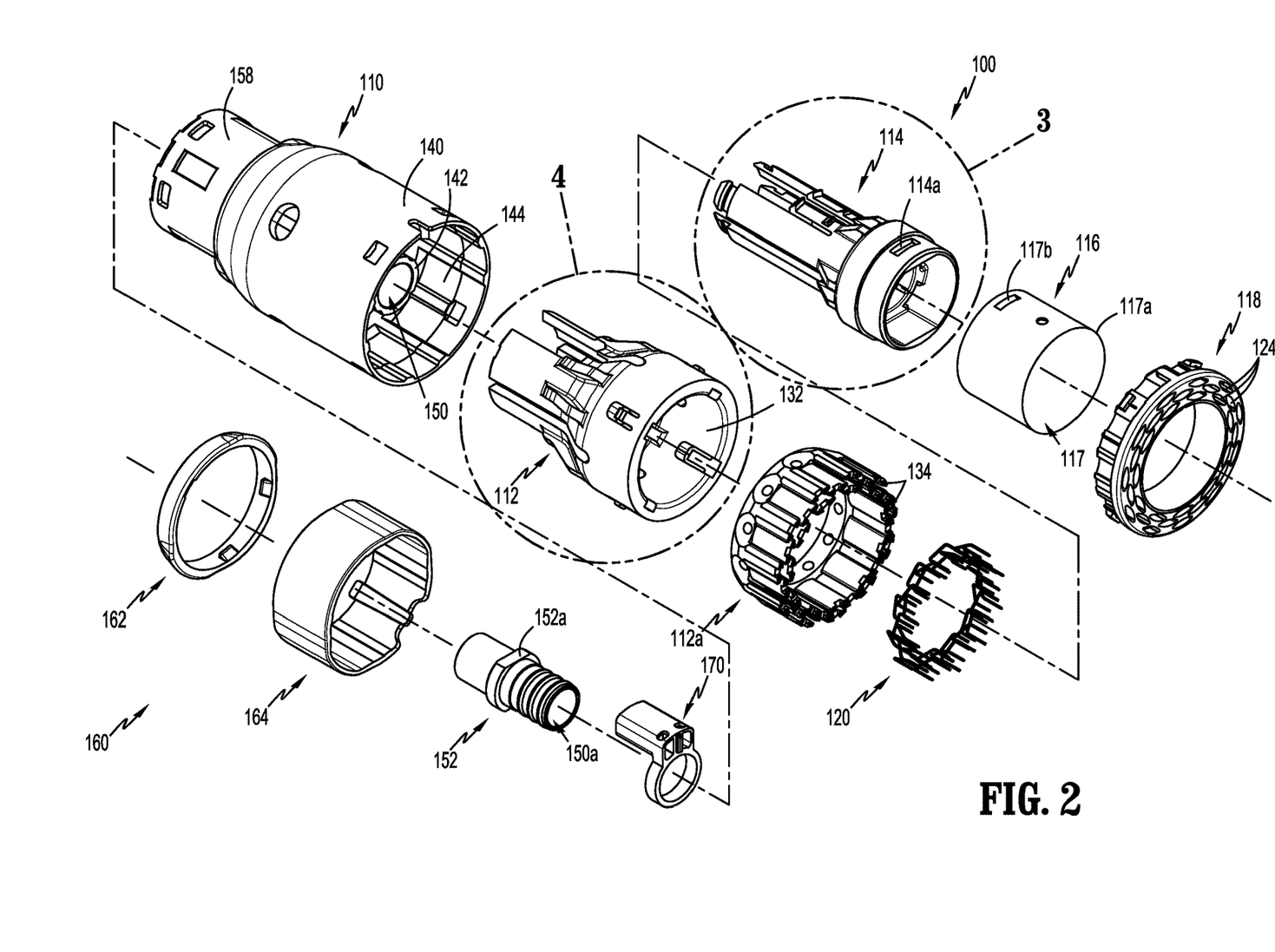
FIG. 2 is a side perspective exploded view of the reload assembly shown in FIG. 1.
Figure 8:
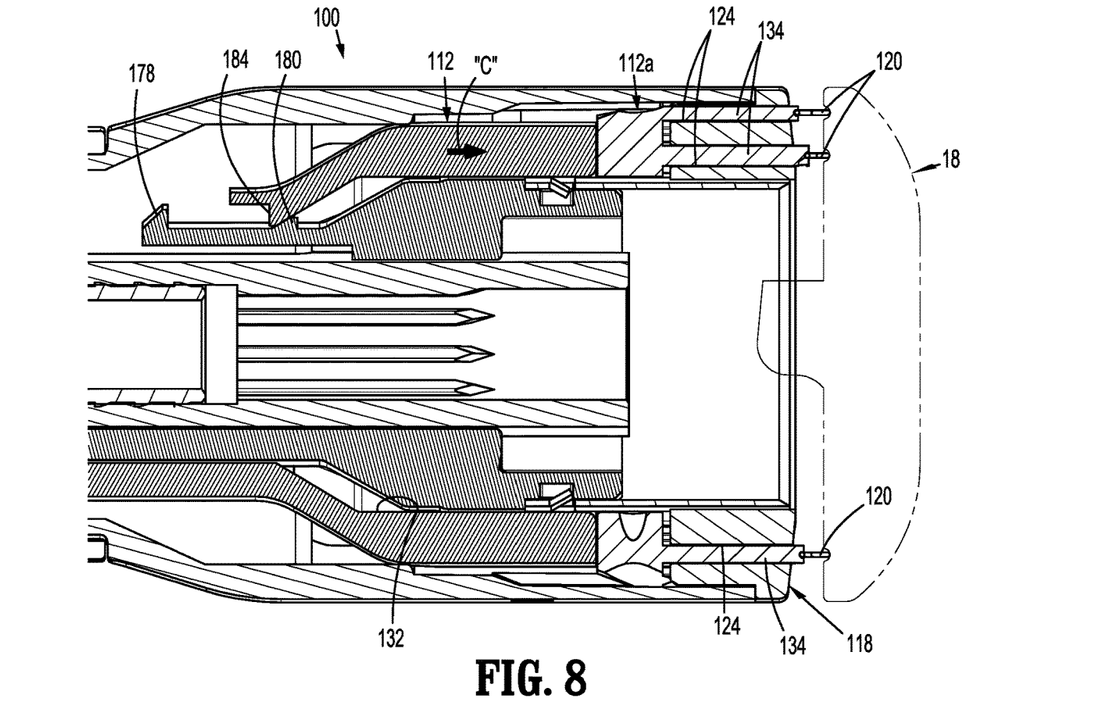
FIG. 8 is a cross-sectional view of the reload shown in FIG. 2 with the staple actuator of the reload assembly in an advanced position.

FIG. 2 illustrates the reload assembly 100 which includes a shell housing 110, a staple actuator 112, a staple pushing member 112a, a knife carrier 114, an annular knife 116 supported on the knife carrier 114, a staple cartridge 118, and a plurality of staples 120 supported within the staple cartridge 118. The staple cartridge 118 is annular and defines annular rows of staple pockets 124. Each of the staple pockets 124 supports one staple of the plurality of staples 120. The staple actuator 112 and the staple pushing member 112a together define a longitudinal through bore 132 (FIG. 8). The staple actuator 112 has a distal portion that abuts a proximal portion of the staple pushing member 112a such that distal movement of the staple actuator 112 within the shell housing 110 causes distal movement of the staple pushing member 112a within the shell housing 110. The staple pushing member 112a of the reload assembly 100 has a plurality of fingers 134. Each of the plurality of fingers 134 is received within a respective one of the staple pockets 124 of the staple cartridge 118 and is movable through the respective staple pocket 124 to eject the staples 120 from the staple pockets 124 when the staple pushing member 112a is moved from a retracted position to an advanced position within the shell housing 110.

The shell housing 110 includes an outer housing portion 140 and an inner housing portion 142 that are spaced from each other to define an annular cavity 144 between the outer and inner housing portions 140 and 142. The staple actuator 112 and the staple pushing member 112a are movable within the annular cavity 144 of the shell housing 110 from retracted positions to advanced positions to eject the staples 120 from the staple cartridge 118.

The annular knife 116 is supported about an outer surface of the knife carrier 114, defines a cylindrical cavity 117, and includes a distal cutting edge 117a. In embodiments, the annular knife 116 includes inwardly extending tangs 117b that are received within pockets 114a defined in an outer surface of the knife carrier 114 to secure the annular knife 116 to the knife carrier 114. The knife carrier 114 and annular knife 116 are positioned within the through bore 132 of the staple actuator 112 and are movable from retracted positions to advanced positions to cut tissue positioned radially inward of the staple cartridge 118.

The inner housing portion 142 of the shell housing 110 defines a through bore 150 (FIG. 3) that receives an anvil shaft (not shown) of the anvil assembly 18. For a more detailed description of an exemplary anvil assembly 18, see, e.g., the '106 patent. The through bore 150 has a proximal portion that receives a bushing 152 (FIG. 5) that defines a through bore 150a that is coaxial and forms an extension of the through bore 150 of the inner housing portion 142. In embodiments, the bushing 152 is formed of a high strength material, e.g., metal, to provide added strength to the inner housing portion 142 of the shell housing 110 and includes an annular flange 152a.

The shell housing 110 includes a proximal portion 158 that supports a coupling mechanism 160 that is operable to releasably couple the reload assembly 100 to the adaptor assembly 14 of the stapling device 10 (FIG. 1). The coupling mechanism 160 allows for removal and replacement of the reload assembly 100 to facilitate reuse of the stapling device 10. In embodiments, the coupling mechanism 160 includes a retaining member 162 and a coupling member 164. The coupling member 164 is received about the proximal portion 158 of the shell housing 110 and is configured to engage the distal portion 14a (FIG. 1) of the adaptor assembly 14 to couple the reload assembly 100 to the adaptor assembly 14. It is envisioned that other coupling mechanisms can be used to secure the reload assembly 100 to the adaptor assembly 14. Alternately, the reload assembly 100 can be non-removably secured to the adaptor assembly 14.

The reload assembly 100 may include an EPROM holder 170 (FIG. 3) that is supported on the shell housing 110 and is configured to support an EPROM (not shown). As is known in the art, an EPROM can communicate with the adaptor assembly 14 to provide information to the adaptor assembly 14 and the handle assembly 12 regarding characteristics of the reload assembly 10. In some embodiments, the EPROM holder 70, may define a cylindrical collar that is received about a distal portion of the bushing 52.

Figures 3, 4:
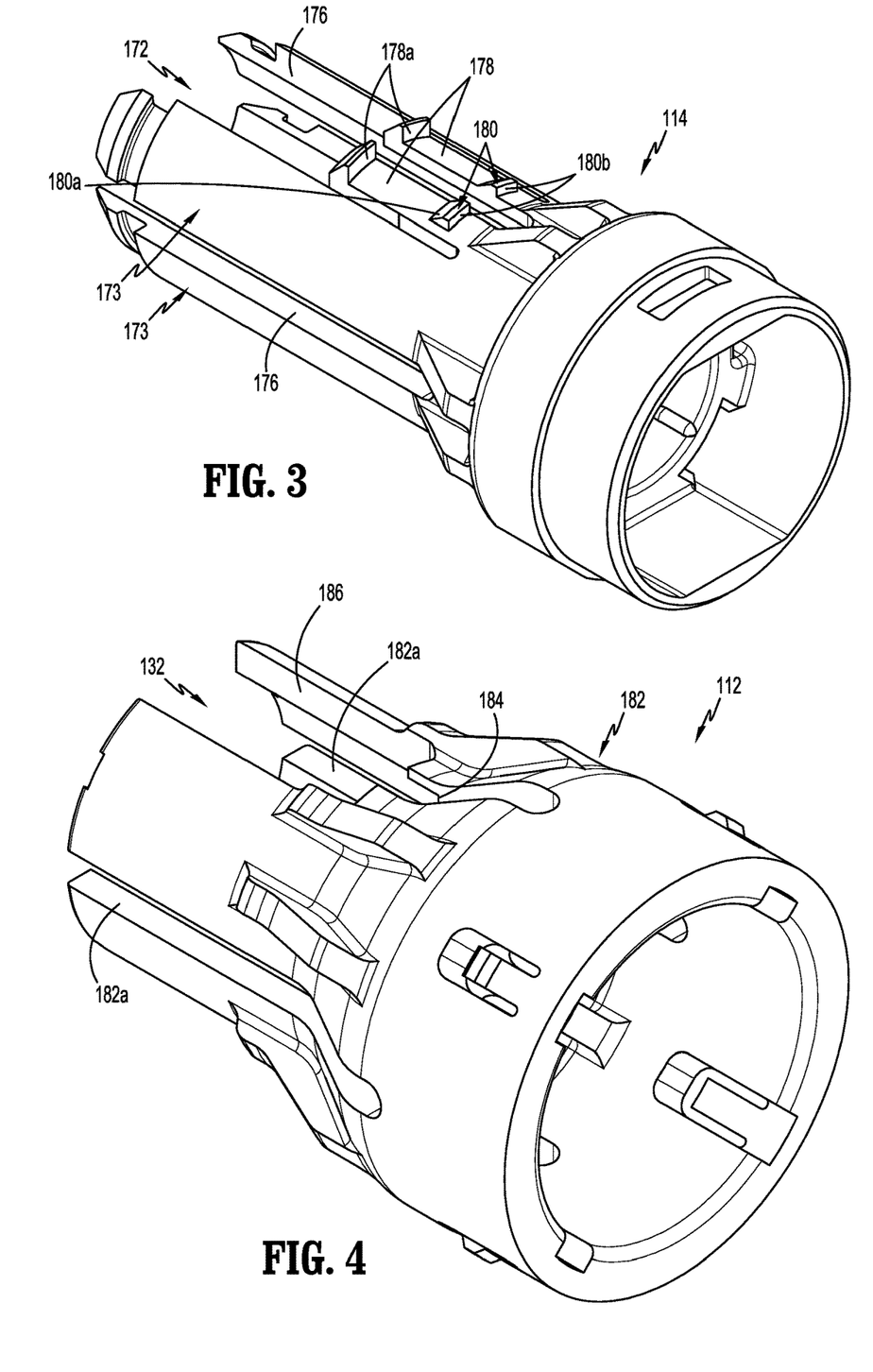
FIG. 3 is a side perspective view from the distal end of a knife carrier of the reload assembly shown in FIG. 2.
FIG. 4 is a side perspective view from the distal end of a staple actuator of the reload assembly shown in FIG. 2.
Figure 9:
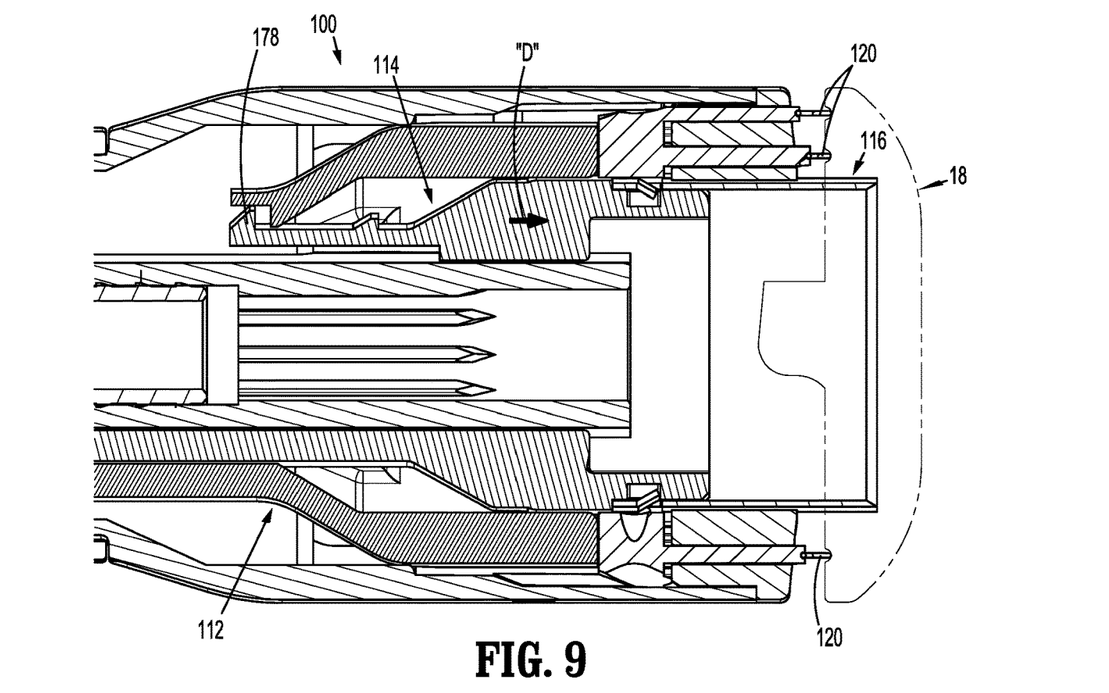
FIG. 9 is a cross-sectional view of the reload shown in FIG. 2 with the knife carrier of the reload assembly in an advanced position.

FIG. 3 illustrates the knife carrier 114 which includes a plurality of spaced resilient longitudinal body portions 173 that are spaced from each other and together define a central bore 172. The central bore 172 of the knife carrier 114 receives the inner housing portion 142 of the shell housing 110 such that the knife carrier 114 is movable about the inner housing portion 142 of the shell housing 110 between a retracted position (FIG. 5) and an advanced position (FIG. 9). The longitudinal body portions 173 of the knife carrier 114 define slots 176 that receive guide portions (not shown) of the shell housing 110 to limit the knife carrier 114 to longitudinal movement within the shell housing 110.

In embodiments, the knife carrier 114 includes hook members 178 that are positioned to engage the staple actuator 112 to move the staple actuator 112 from its retracted position to its advanced position. The hook members 178 extend radially outwardly from the knife carrier 114 towards the staple actuator 112 within the annular cavity 144 (FIG. 2) of the shell housing 110. Each of the hook members 178 includes an engagement surface 178a and supports a locking tab 180. The locking tabs 180 are positioned distally of the engagement surfaces 178a of the hook members 178 and extend radially outwardly from the knife carrier 114 towards the staple actuator 112. Each of the locking tabs 180 includes a proximal facing angled surface 180a and a distal facing locking surface 180b.

FIG. 4 illustrates the staple actuator 112 which includes a body 182 that is also received about the inner housing portion 142 (FIG. 3) of the shell housing 110 and is movable from a retracted position (FIG. 5) to an advanced position (FIG. 9) in response to movement of the knife carrier 114 from its retracted position to its advanced position. The body 182 defines a plurality of guide slots 182a and at least one stop surface 184. In some embodiments, the at least one stop surface 184 is positioned at a distal end of a channel 186 formed in the body 182. The channel 186 is positioned and dimensioned to receive the hook members 178. The guide slots 182a of the staple actuator 112 receive the guide members (not shown) of the shell housing 110 to limit the staple actuator 112 to longitudinal movement within the shell housing 110. The at least one stop surface 184 of the staple actuator 112 is longitudinally aligned with the engagement surfaces 178a of the hook members 178 (FIG. 3) of the knife carrier 114 such that advancement of the knife carrier 114 within the through bore 132 of the staple actuator 112 causes the engagement surfaces 178a of the hook members 178 of the knife carrier 112 to engage the at least one stop surface 184 of the staple actuator 112. In this manner, the engagement of the engagement surfaces 178a of the hook members 178 with the stop surfaces 184 of the staple actuator 112 prior to advancement of the staple actuator 112 prevents advancement of the knife carrier 114. Alternatively, the staple actuator 112 and the knife carrier 114 may configured such that advancement of the knife carrier 114 advances the staple actuator 112 within the shell housing 110 to its advanced position to complete the staple forming process.

Figure 5:
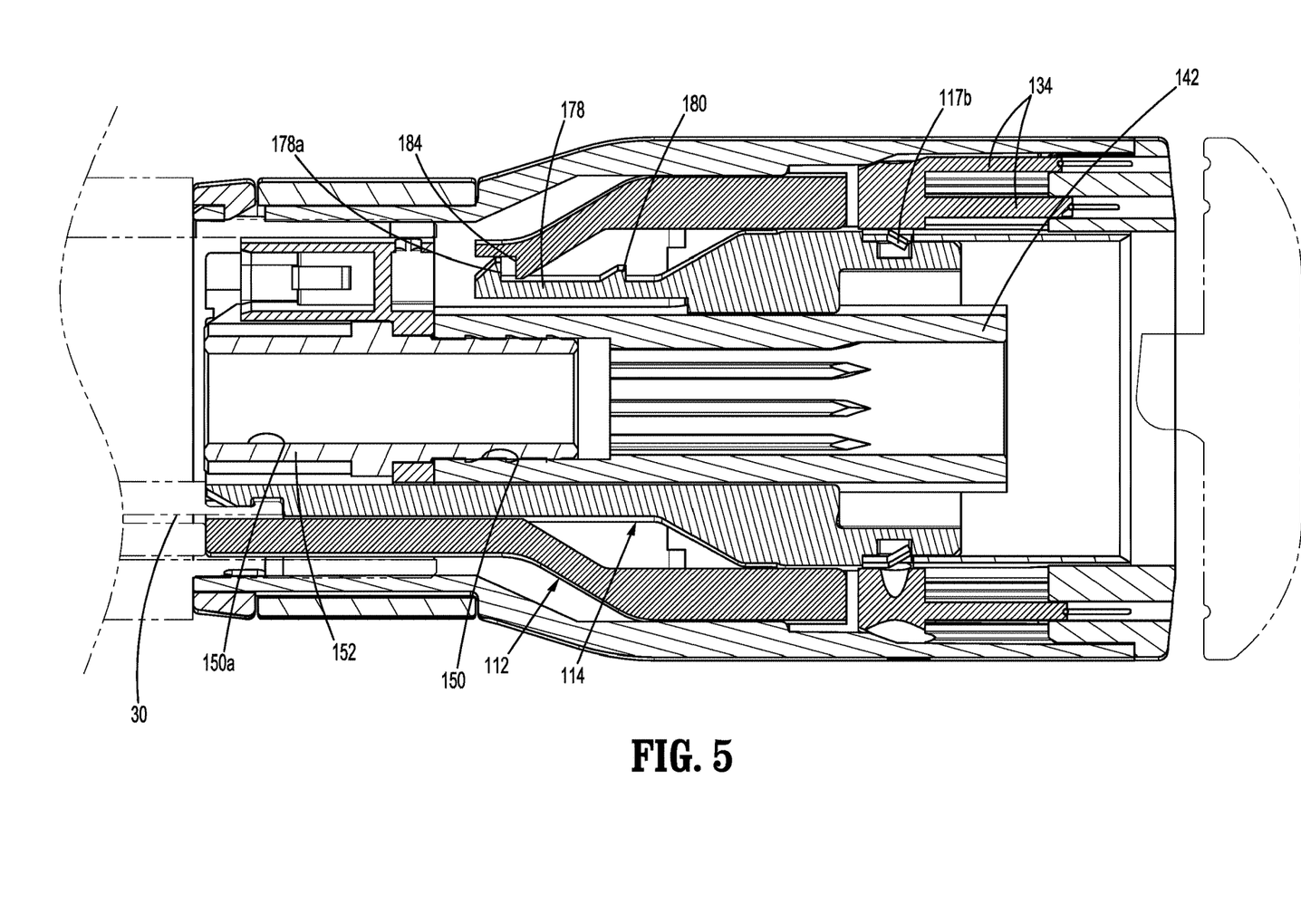
FIG. 5 is a cross-sectional view of the reload shown in FIG. 2 with the reload assembly in a pre-fired state.

FIG. 5 illustrates the reload assembly 100 in a pre-fired condition with the knife carrier 114 and staple actuator 112 of the reload assembly 100 (FIG. 3) in retracted positions. When the knife carrier 114 and the staple actuator 112 are in pre-fired retracted positions, the engagement surface 178a of each of the hook members 178 is aligned with and spaced slightly proximally of the respective stop surface 184 of the staple actuator 112 and each of the locking tabs 180 is positioned distally of a respective stop surface 184.

Figure 6:
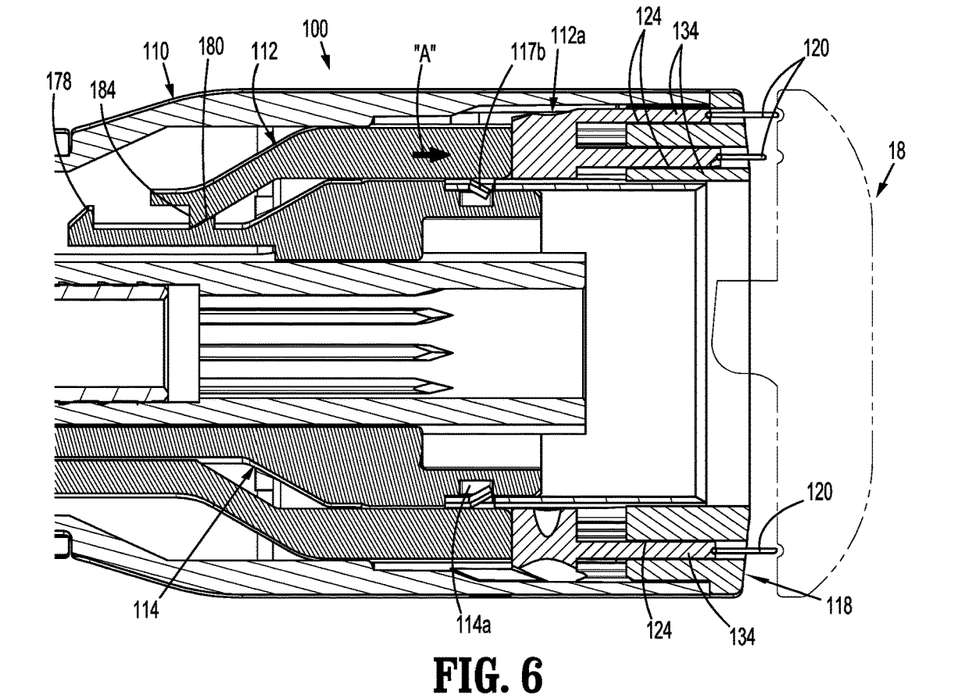
FIG. 6 is a cross-sectional view of the reload shown in FIG. 2 with the staple actuator of the reload assembly in a partially advanced position.

FIG. 6 illustrates the reload assembly 100 as the staple actuator 112 is moved to a partially advanced position independently of the knife carrier 114. As the staple actuator 112 moves distally within the shell housing 110, the staple pushing member 112a is moved distally in the direction indicated by arrow "A" to advance the plurality of fingers 134 of the staple pushing member 112a into the staple pockets 124 of the staple cartridge 118 to partially eject the staples 120 from the staple cartridge 118 into the anvil assembly 18. In the partially advanced position, the stop surface 184 is positioned immediately proximal of the locking tabs 180 and engagement surfaces 178a of the hook members 178 are spaced proximally of the stop surface 184 of the of the staple actuator 112.

Figure 7:
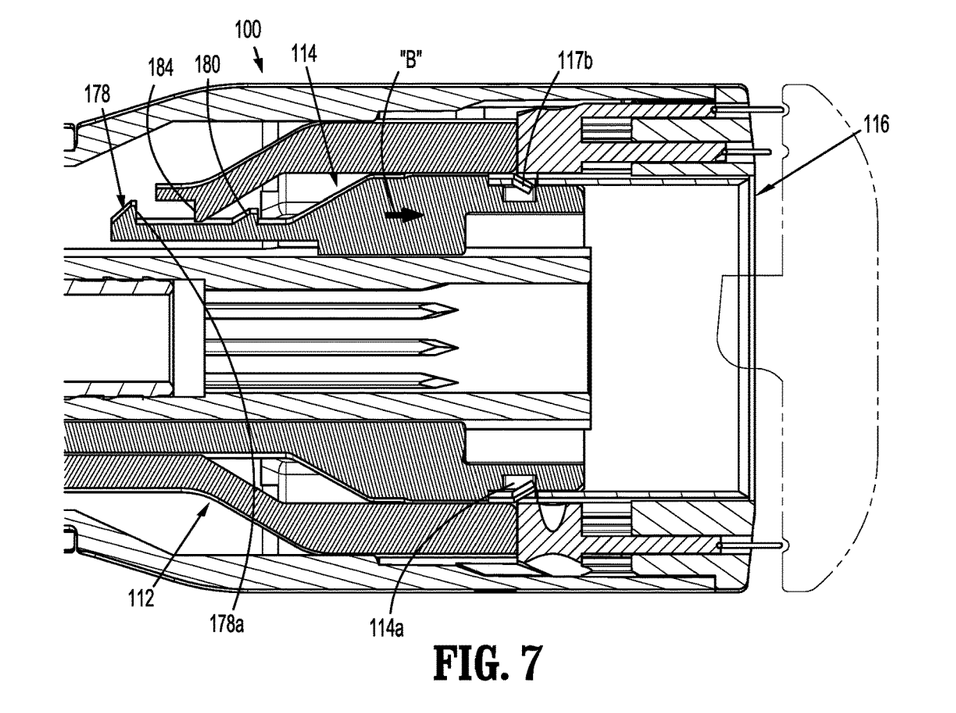
FIG. 7 is a cross-sectional view of the reload shown in FIG. 2 with the knife carrier of the reload assembly in a partially advanced position.

FIG. 7 illustrates the reload assembly 100 as the knife carrier 114 is moved independently of the staple actuator 112 to a partially advanced position. To prevent the knife carrier 114 from being prematurely locked out, and thereby preventing the knife carrier 114 from being moved to its advanced position to cut tissue, subsequent to the staple actuator 112 being moved to its advanced position, the knife carrier 114 is moved distally by a knife carrier driver 30 (FIG. 5) of the stapling device 10 (FIG. 1) in the direction indicated by arrow "B" to a partially advanced position. In this manner, the locking tabs 180 of the knife carrier 114 are moved to a position spaced further distally of the stop surface 184 of the staple actuator 112 to permit subsequent movement of the knife carrier 114 and the attached annular knife 116 to its advanced position.

FIG. 8 illustrates the reload assembly 100 as the staple actuator 112 is moved from its partially advanced position to its fully advanced position independently of the knife carrier 114. As the staple actuator 112 moves distally within the shell housing 110, the staple pushing member 112a is moved distally in the direction indicated by arrow "C" to advance the plurality of fingers 134 of the staple pushing member 112a further through the staple pockets 124 of the staple cartridge 118 to eject the staples 120 from the staple cartridge 118 into the anvil assembly 18 to form the staples 120 in tissue (not shown). In the fully advanced position of the staple actuator 112, the stop surface 184 of the staple actuator 112 is positioned immediately proximal of the locking tabs 180 of the knife carrier 114.

FIG. 9 illustrates the reload assembly 100 as the knife carrier 114 is moved to its fully advanced position independently of the staple actuator 112 with the staple actuator 112 in its fully advanced position. As illustrated, the annular knife 116 which is secured to the knife carrier 114 is moved distally with the knife carrier 114 in the direction indicated by arrows "D" to cut tissue clamped between the anvil 18 and the staple cartridge 118. When the staple actuator 112 and the knife carrier 114 are both in their fully advanced positions, the engagement surfaces 178a of the hook members 178 are positioned proximally of the stop surface 184 and the stop surface 184 of the staple actuator 112 is spaced proximally of the locking tabs 180 of the knife carrier 114.

Although shown and illustrated as separate actions, it is envisioned that the staple actuator 112 and the knife carrier 114 may be moved simultaneously, as long as the locking tabs 180 of the knife carrier 114 remain located distal of the stop surface 184 of the staple actuator 112.

Figure 10:
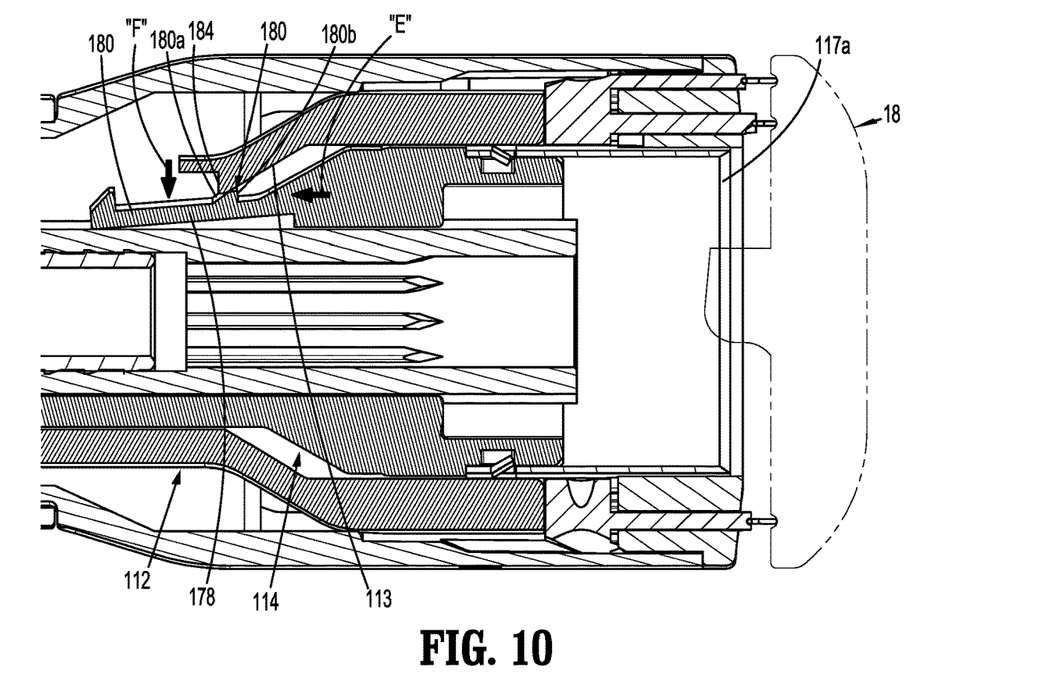
FIG. 10 is a cross-sectional view of the reload shown in FIG. 2 with the knife carrier of the reload assembly in a partially retracted position.
Figure 11:
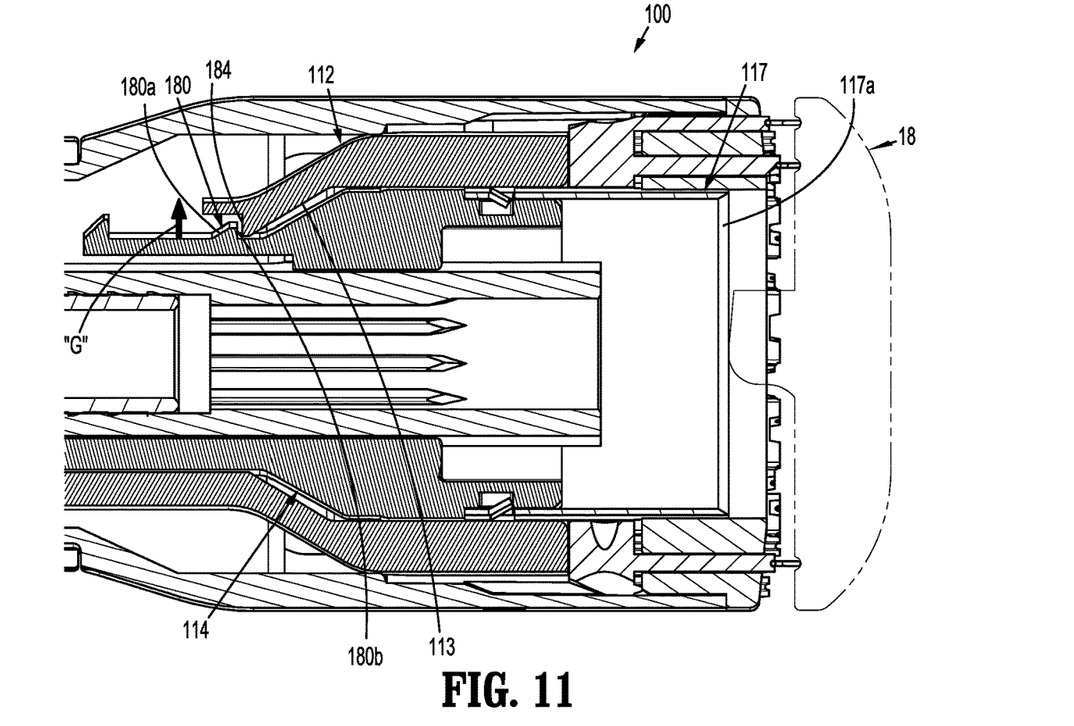
FIG. 11 is a cross-sectional view of the reload shown in FIG. 2 with the knife carrier of the reload assembly in a retracted position.

FIGS. 10 and 11 illustrate the reload assembly 100 as the knife carrier 114 is moved from its advanced position to its retracted position independently of the staple actuator 114 after the reload assembly 100 is fired. When the knife carrier 114 is moved proximally in the direction indicated by arrows "E" towards its retracted position, the annular knife 116 is also moved proximally to a position shielded within the shell housing 110. In this position, a clinician is protected from inadvertent injury caused by the cutting edge 117a of the annular knife 116. As the knife carrier 114 and annular knife 116 are moved proximally within the shell housing 110, the staple actuator 112 remains in its advanced position within the shell housing 110. As the knife carrier 114 moves proximally in relation to the staple actuator 112, the angled surface 180a of each of the locking tabs 180 engage an angled inner surface 113 of the staple actuator 112 such that the hook members 178 are deformed inwardly away from the staple actuator 112 in the direction indicated by arrow "F" in FIG. 10. In their deformed state, the locking tabs 180 of the knife carrier 114 pass inwardly and move proximally beyond the respective stop surfaces 184 (FIG. 11) of the staple actuator 112. When the locking tabs 180 move proximally past the respective stop surfaces 184, the locking tabs 180 spring outwardly to their undeformed state in the direction indicated by arrow "G" in FIG. 11 to positions aligned with the respective stop surfaces 184. In this position, the locking tabs 180 prevent readvancement of the knife carrier 112 to retain the annular knife 116 within the shell housing 110 of the reload assembly 100.

Figure 12:
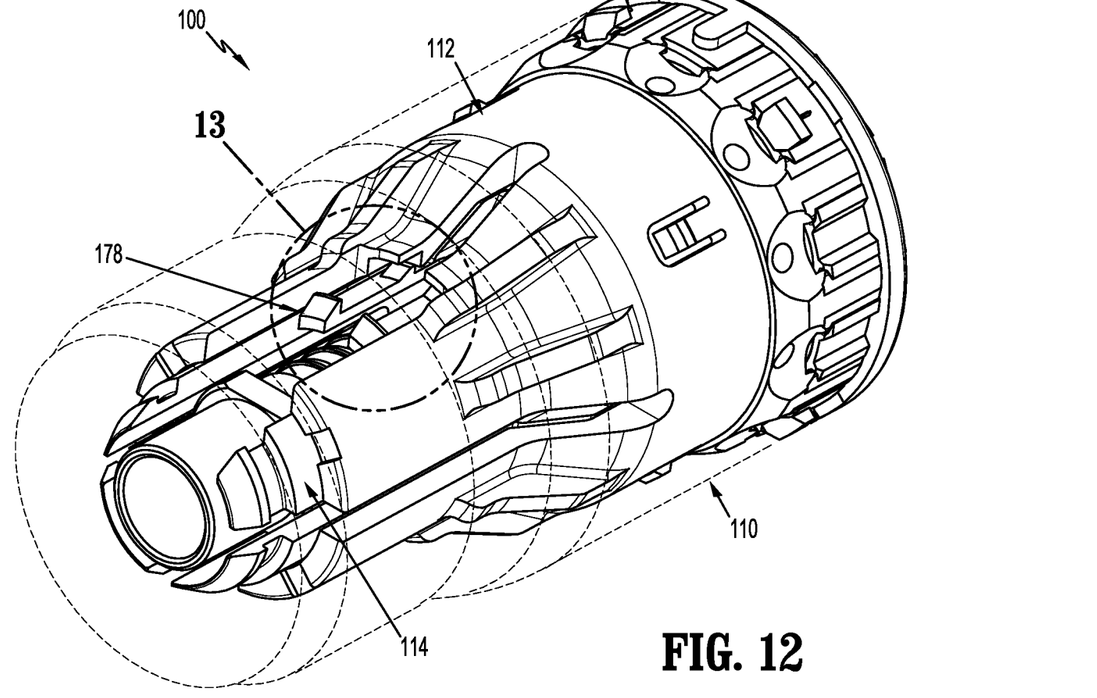
FIG. 12 is a perspective view from the proximal end of the reload assembly shown in FIG. 2 with the shell assembly shown in phantom and the knife carrier in the retracted position.
Figure 13:
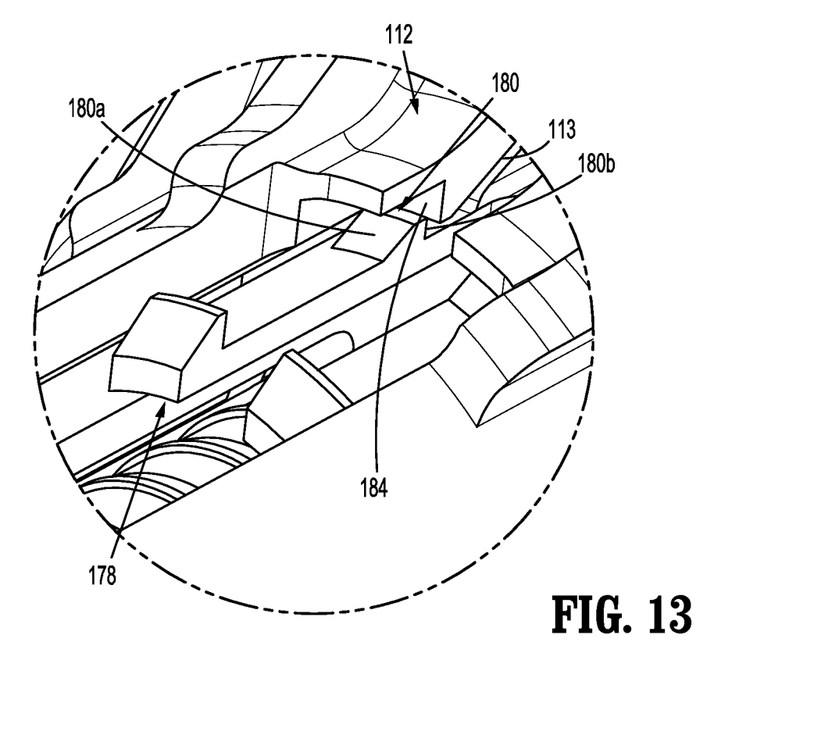
FIG. 13 is an enlarged view of the indicated area of detail shown in FIG. 12.

FIGS. 12 and 13 illustrate the reload assembly 100 in the post fired condition. In the post fired condition, the stapler actuator 112 the knife carrier 114, including the annular knife 116 (FIG. 11), is retained in its retracted position by the stop surfaces 184. More particularly, the locking tabs 180 of the knife carrier 114 are positioned proximal of the stop surface 184 of the staple actuator 112 to prevent advancement of the knife carrier 114.

Persons skilled in the art will understand that the devices and methods specifically described herein and illustrated in the accompanying drawings are non-limiting exemplary embodiments. It is envisioned that the elements and features illustrated or described in connection with one exemplary embodiment may be combined with the elements and features of another without departing from the scope of the disclosure. As well, one skilled in the art will appreciate further features and advantages of the disclosure based on the above-described embodiments. Accordingly, the disclosure is not to be limited by what has been particularly shown and described, except as indicated by the appended claims.

What is claimed is:

1. A surgical stapling device comprising:
an adaptor assembly having a proximal end portion and a distal end portion; and
a reload assembly supported on the distal end portion of the adaptor assembly, the reload assembly including:
a shell housing including an outer housing portion and an inner housing portion, the inner and outer housing portions defining an annular cavity therebetween;
a staple cartridge supporting a plurality of staples supported on the shell housing;
a staple pusher supported within the annular cavity and movable from a staple pusher retracted position to a staple pusher advanced position to eject staples from the staple cartridge;
a staple actuator supported within the annular cavity and having a stop surface, the staple actuator positioned to engage the staple pusher and movable from a staple actuator retracted position to a stapler actuator advanced position to move the staple pusher from the staple pusher retracted position to the staple pusher advanced position, the staple actuator and the staple pusher defining a through bore;
a knife carrier supported within the through bore and movable between a knife carrier retracted position and a knife carrier advanced position, the knife carrier defining a longitudinal axis and including at least one locking tab, the at least one locking tab positioned distal of the stop surface of the staple actuator when the knife actuator is in the knife actuator advanced position and positioned proximal proximally of the stop surface on the staple actuator when the staple actuator is in the staple actuator advanced position and the knife carrier is in the knife carrier retracted position to prevent readvancement of the knife carrier; and
a knife supported on the knife carrier.

2. The surgical stapling device of claim 1, further including a handle assembly, the proximal end portion of the adaptor assembly being supported on the handle assembly.

3. The surgical stapling device of claim 1, wherein the at least one locking tab of the knife carrier is positioned distally of the stop surface of the staple actuator when the staple actuator is in the staple actuator retracted position and the knife carrier is in the knife carrier retracted position.

4. The surgical stapling device of claim 1, wherein the knife carrier includes at least one hook member, the at least one hook member being aligned with the stop surface of the staple actuator such that the staple actuator maintains the knife carrier within the shell housing.

5. The surgical stapling device of claim 1, wherein the knife carrier includes at least one hook member, the at least one hook member being aligned with the stop surface of the staple actuator to prevent advancement of the knife carrier prior to advancement of the staple actuator.

6. The surgical stapling device of claim 1, further including a coupling mechanism, the coupling mechanism coupling the reload assembly to the adaptor assembly to facilitate release of the reload assembly from the adaptor assembly.

7. The surgical stapling device of claim 1, wherein the knife carrier includes at least one hook member having a proximal end, the at least one locking tab being disposed on the at least one hook member distal of the proximal end.

8. The surgical stapling device of claim 7, wherein the at least one locking tab includes an angled surface and the staple actuator includes an angled inner surface, wherein engagement of the angled surface of the at least one locking tab with the angled inner surface of the staple actuator deflects the at least one hook member radial inward.

9. The surgical stapling device of claim 8, wherein the at least one locking tab includes a locking surface, engagement of the stop surface with the locking surfaces prevents advancement of the knife carrier.

10. A reload assembly for a surgical stapling device, the reload assembly comprising:
a shell housing including an outer housing portion and an inner housing portion, the inner and outer housing portions defining an annular cavity therebetween;
a staple cartridge supporting a plurality of staples supported on the shell housing;
a staple pusher supported within the annular cavity and movable from a staple pusher retracted position to a staple pusher advanced position to eject staples from the staple cartridge;
a staple actuator supported within the annular cavity and having a stop surface, the staple actuator positioned to engage the staple pusher and movable from a staple actuator retracted position to a staple actuator advanced position to move the staple pusher from the staple pusher retracted position to the staple pusher advanced position, the staple actuator and the staple pusher defining a through bore;
a knife carrier supported within the through bore and movable between a knife carrier retracted position and a knife carrier advanced position, the knife carrier defining a longitudinal axis and including at least one locking tab, the at least one locking tab positioned distal of the stop surface of the staple actuator when the knife actuator is in the knife actuator advanced position and positioned proximal of the stop surface on the staple actuator when the staple actuator is in the staple actuator advanced position and the knife carrier is in the knife carrier retracted position to prevent readvancement of the knife carrier; and
a knife supported on the knife carrier.

11. The reload assembly of claim 10, wherein the knife carrier includes at least one hook member, the at least one hook member being aligned with the stop surface of the staple actuator such that the staple actuator maintains the knife carrier within the shell housing.

12. The reload assembly of claim 10, wherein the knife carrier includes at least one hook member, the at least one hook member being aligned with the stop surface of the staple actuator to prevent advancement of the knife carrier prior to advancement of the staple actuator.

13. The reload assembly of claim 10, further including a coupling mechanism configured to couple the reload assembly to an adaptor assembly of the surgical stapling device to facilitate release of the reload assembly from the adaptor assembly.

14. The reload assembly of claim 10, wherein the knife carrier includes at least one hook member having a proximal end, the at least one locking tab being disposed on the at least one hook member distal of the proximal end.

15. The reload assembly of claim 14, wherein the at least one locking tab includes an angled surface and the staple actuator includes an angled inner surface, wherein engagement of the angled surface of the at least one locking tab with the angled inner surface of the staple actuator deflects the at least one hook member radial inward.

16. The reload assembly of claim 15, wherein the at least one locking tab includes a locking surface, engagement of the stop surface with the locking surfaces prevents advancement of the knife carrier.

17. The reload assembly of claim 15, wherein the at least one locking tab is positioned distally of the stop surface on the staple actuator when the staple actuator is in the staple actuator retracted position to permit advancement of the knife carrier.

18. A surgical stapling device comprising:
a handle assembly;
an adaptor assembly having a proximal end portion and a distal end portion, the proximal end portion being configured for releasable connection to the handle assembly; and
a reload assembly supported on the distal end portion of the adaptor assembly, the reload assembly including:
a shell housing including an outer housing portion and an inner housing portion, the inner and outer housing portions defining an annular cavity therebetween;
a staple cartridge supporting a plurality of staples supported on the shell housing;
a staple pusher supported within the annular cavity and movable from a staple pusher retracted position to a staple pusher advanced position to eject staples from the staple cartridge;
a staple actuator supported within the annular cavity and having a stop surface, the staple actuator positioned to engage the staple pusher and movable from a staple actuator retracted position to a staple actuator advanced position to move the staple pusher from the staple pusher retracted position to the staple pusher advanced position, the staple actuator and the staple pusher defining a through bore;
a knife carrier supported within the through bore and movable between a knife carrier retracted position and a knife carrier advanced position, the knife carrier defining a longitudinal axis and including at least one locking tab, the at least one locking tab positioned distal of the stop surface of the staple actuator when the knife actuator is in the knife actuator advanced position and positioned proximal of the stop surface on the staple actuator when the staple actuator is in the staple actuator advanced position and the knife carrier is in the knife carrier retracted position to prevent readvancement of the knife carrier; and a knife supported on the knife carrier.

19. The surgical stapling device of claim 18, wherein the at least one locking tab is positioned distally of the stop surface on the staple actuator when the staple actuator is in the staple actuator retracted position to permit advancement of the knife carrier.

20. The surgical stapling device of claim 18, wherein the knife carrier includes at least one hook member, the at least one hook member being aligned with the stop surface of the staple actuator such that the staple actuator maintains the knife carrier within the shell housing.

* * * * *